(12) United States Patent
Robinson

(10) Patent No.: US 11,241,352 B2
(45) Date of Patent: Feb. 8, 2022

(54) CONTOURED URINAL ASSEMBLY

(71) Applicant: Ora Robinson, Colton, CA (US)

(72) Inventor: Ora Robinson, Colton, CA (US)

( * ) Notice: Subject to any disclaimer, the term of this patent is extended or adjusted under 35 U.S.C. 154(b) by 145 days.

(21) Appl. No.: 16/448,058

(22) Filed: Jun. 21, 2019

(65) Prior Publication Data
US 2020/0397636 A1    Dec. 24, 2020

(51) Int. Cl.
*A61G 9/00*    (2006.01)
*A61F 5/453*    (2006.01)

(52) U.S. Cl.
CPC ............. *A61G 9/006* (2013.01); *A61F 5/453* (2013.01)

(58) Field of Classification Search
CPC ................................ A61G 9/006; A61F 5/453
See application file for complete search history.

(56) References Cited

U.S. PATENT DOCUMENTS

| 622,631 | A | * | 4/1899 | Oberton | A61G 9/006 |
| | | | | | 4/144.3 |
| 3,727,244 | A | | 4/1973 | Collins | |
| 4,309,779 | A | | 1/1982 | Knight | |
| 4,665,571 | A | | 5/1987 | Muccione | |
| 4,769,858 | A | * | 9/1988 | Gamm | A61G 9/006 |
| | | | | | 215/380 |
| D389,240 | S | | 1/1998 | Corona | |
| 6,026,519 | A | | 2/2000 | Kaluza | |
| 6,941,587 | B1 | * | 9/2005 | Fletcher | A61G 9/006 |
| | | | | | 4/144.1 |
| 7,845,026 | B2 | | 12/2010 | Brown | |
| 9,622,930 | B2 | | 4/2017 | Sands | |
| 9,629,771 | B2 | * | 4/2017 | Knowlton | A61G 9/006 |

OTHER PUBLICATIONS

"Gasket." Merriam-Webster.com Dictionary, Merriam-Webster, https://www.merriam-webster.com/dictionary/gasket. Accessed Jan. 28, 2021.*

* cited by examiner

*Primary Examiner* — Philip R Wiest
*Assistant Examiner* — Gregory J Feulner

(57) ABSTRACT

A contoured urinal assembly for enhancing comfort for a user during urine collection includes a bottle that has an angled neck to facilitate a user to insert the user's penis into the angled neck for urine collection. A handle is coupled to the bottle for gripping. A ring extends around the bottle and the ring is comprised of a resiliently compressible material to enhance comfort for the user. A saddle is coupled to the ring. The penis is positioned on the saddle to inhibit the penis from being abraded. Additionally, the saddle extends into the bottle to direct the penis into the bottle for urine collection.

5 Claims, 5 Drawing Sheets

CONTOURED URINAL ASSEMBLY

BACKGROUND OF THE INVENTION

(1) Field of the Invention

The disclosure and prior art relates to urinal devices and more particularly pertains to a new urinal device for enhancing comfort for a user during urine collection.

BRIEF SUMMARY OF THE INVENTION

An embodiment of the disclosure meets the needs presented above by generally comprising a bottle that has an angled neck to facilitate a user to insert the user's penis into the angled neck for urine collection. A handle is coupled to the bottle for gripping. A ring extends around the bottle and the ring is comprised of a resiliently compressible material to enhance comfort for the user. A saddle is coupled to the ring. The penis is positioned on the saddle to inhibit the penis from being abraded. Additionally, the saddle extends into the bottle to direct the penis into the bottle for urine collection.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
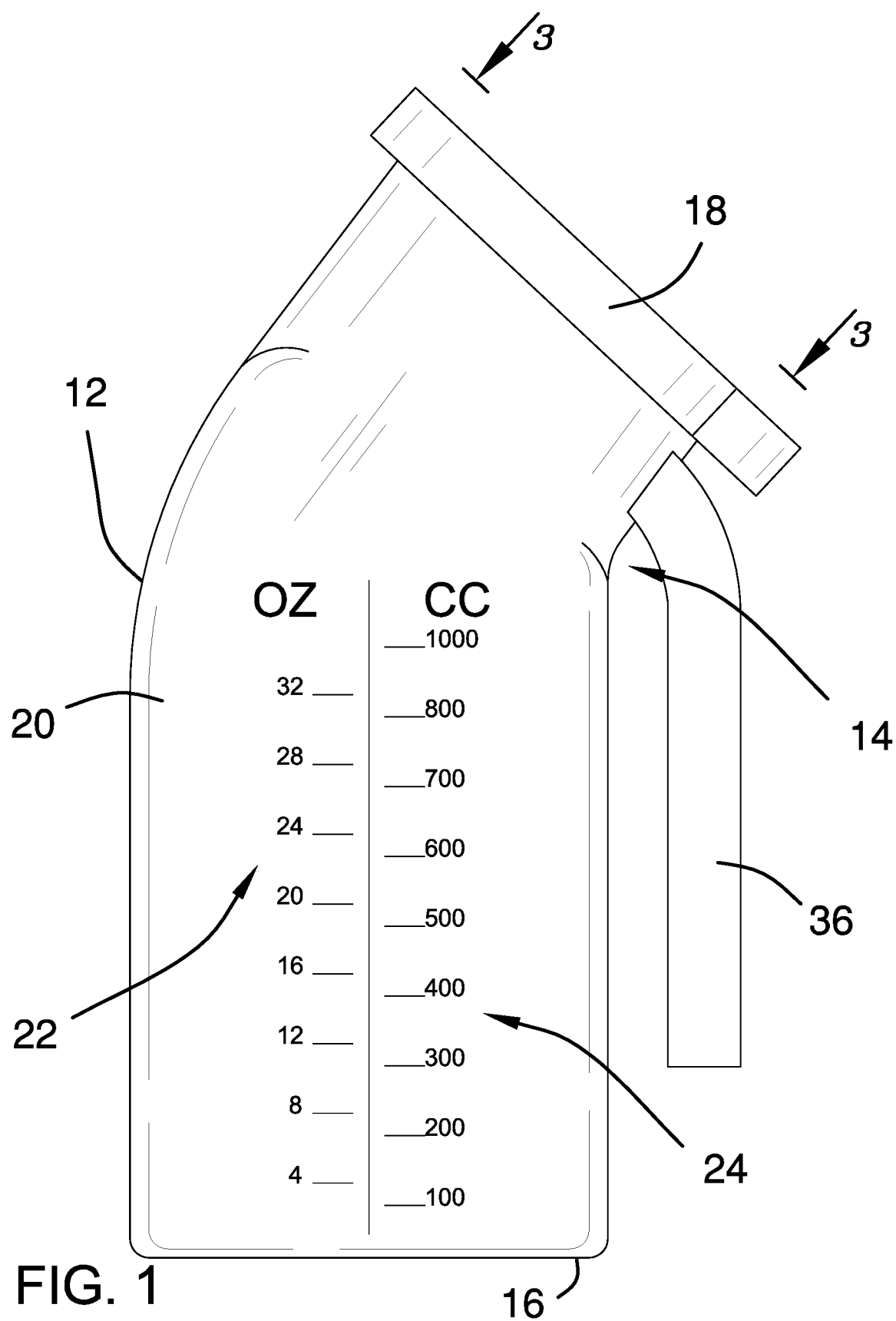
FIG. 1 is a right side view of a contoured urinal assembly according to an embodiment of the disclosure.
Figure 2:
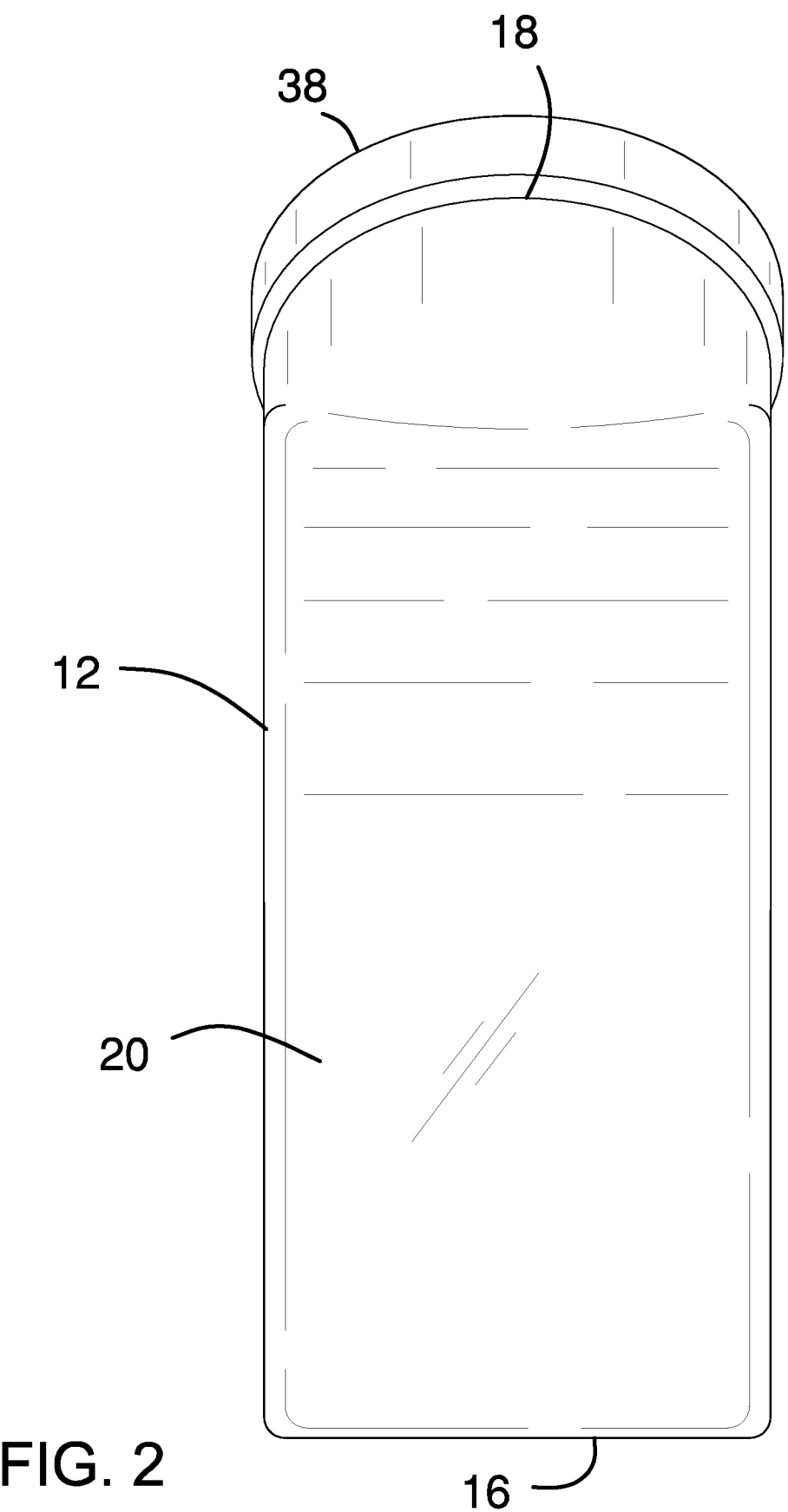
FIG. 2 is a back view of an embodiment of the disclosure.
Figure 3:
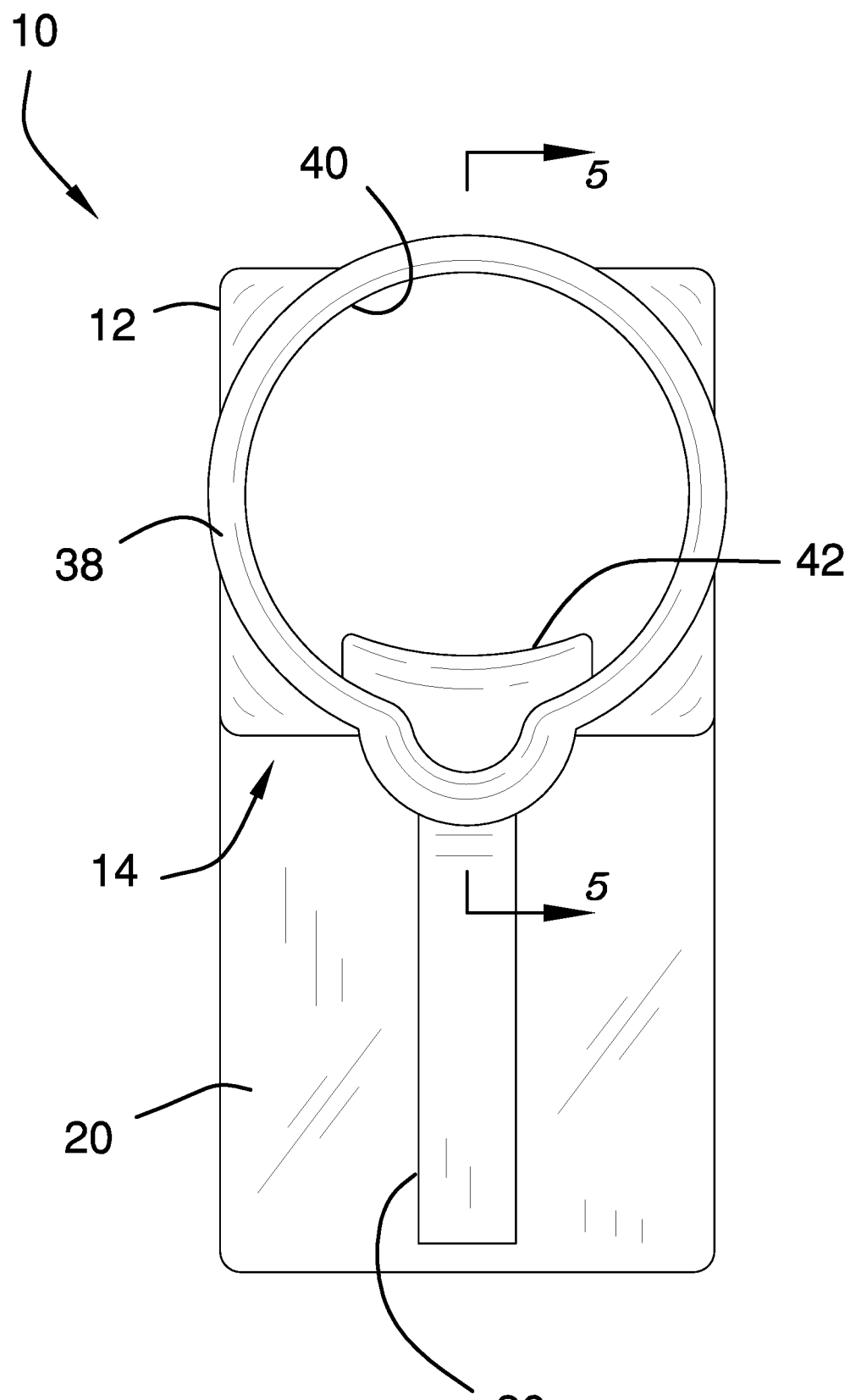
FIG. 3 is a front view of an embodiment of the disclosure.
Figure 4:
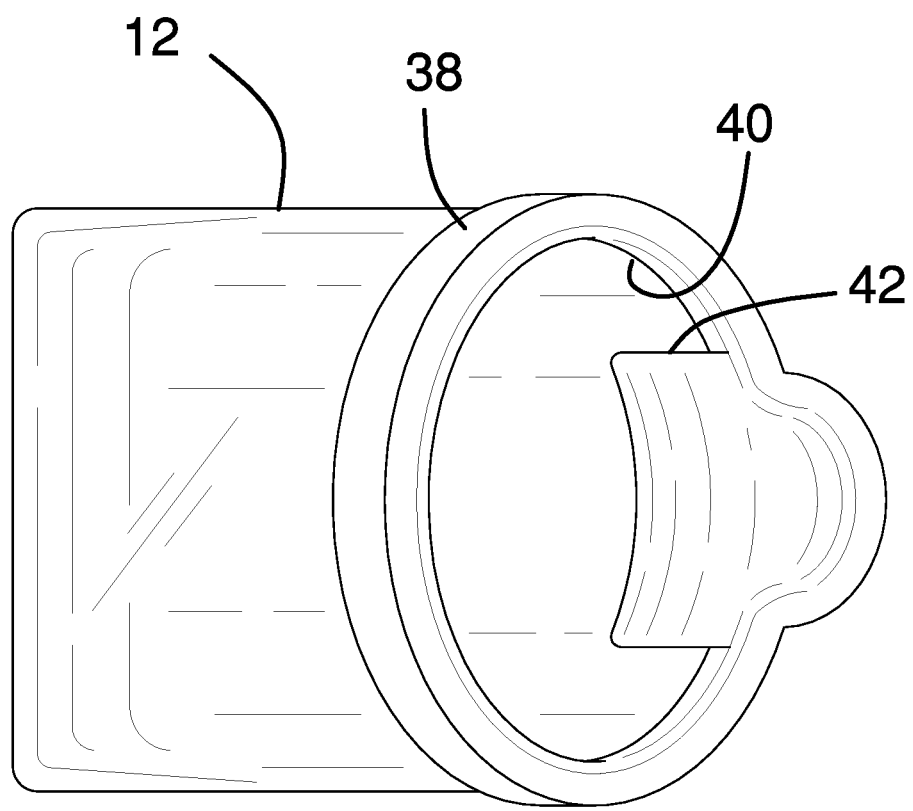
FIG. 4 is a top view of an embodiment of the disclosure.
Figure 5:
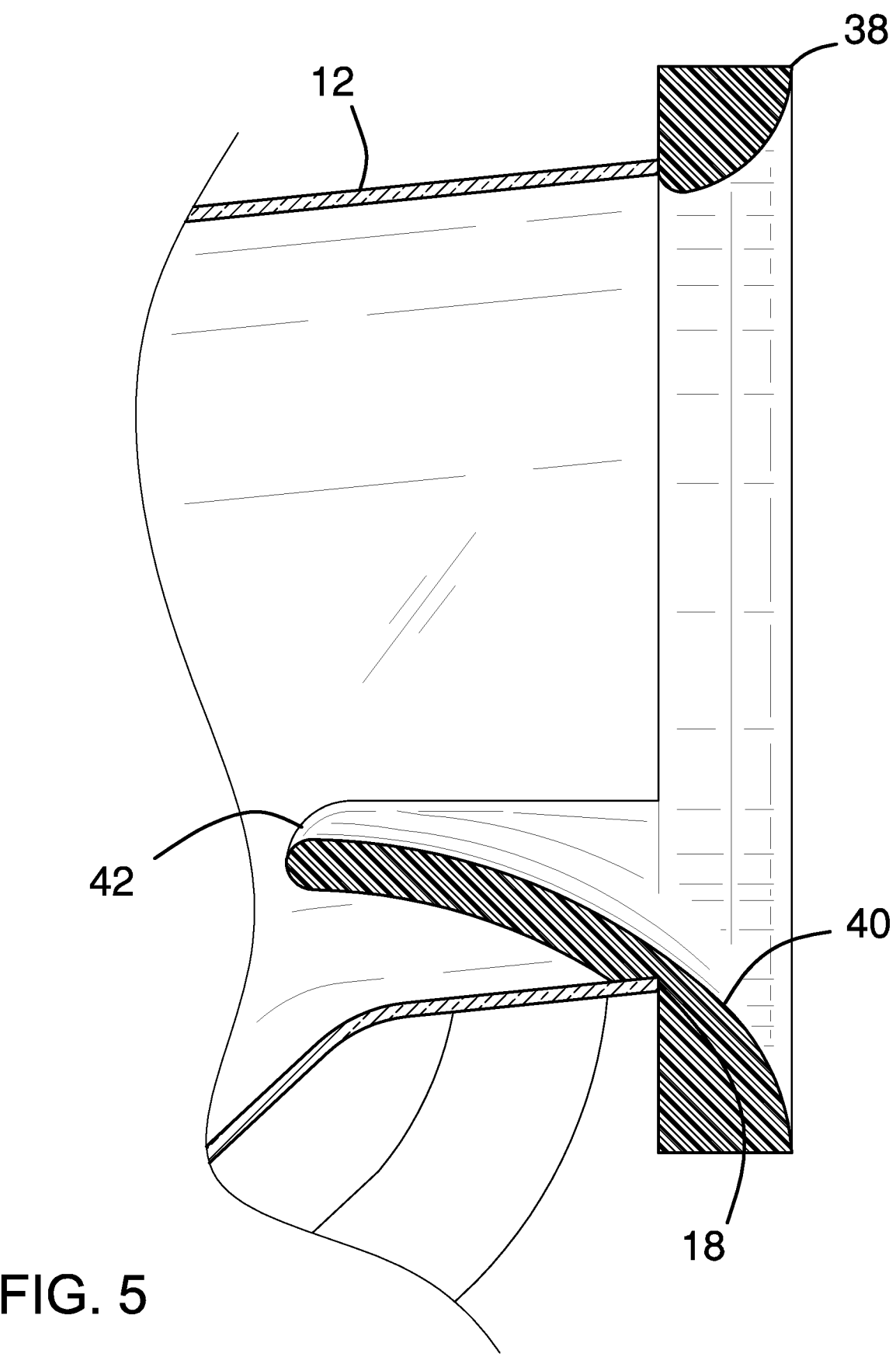
FIG. 5 is a cross sectional view taken along line 5-5 of FIG. 3 of an embodiment of the disclosure.

With reference now to the drawings, and in particular to FIGS. 1 through 5 thereof, a new urinal device embodying the principles and concepts of an embodiment of the disclosure and generally designated by the reference numeral 10 will be described.

As best illustrated in FIGS. 1 through 5, the contoured urinal assembly 10 generally comprises a bottle 12 that has an angled neck 14. The angled neck 14 facilitates a user to insert the user's penis into the angled neck 14 for urine collection. The bottle 12 has a bottom end 16, a top end 18 and an outer wall 20 extending therebetween. The top end 18 is open into an interior of the bottle 12 and the penis can be positioned in the top end 18. The outer wall 20 is curved between the bottom end 16 and the top end 18 such that the top end 18 lies on a plane that is angled with the bottom end 16.

The outer wall 20 has ounces indicia 22 printed thereon comprising a graduated scale for measuring 38 fluid volume in fluid ounces. Additionally, the outer wall 20 has cubic centimeter indicia 24 printed thereon comprising a graduated scale for measuring 38 fluid volume in cubic centimeters. The bottle 12 may have a fluid capacity of approximately 900 ml. A handle 36 is coupled to the bottle 12 for gripping. The handle 36 extends away from the outer wall 20 of the bottle 12. Additionally, the handle 36 extends toward the bottom end 16 of the bottle 12.

A ring 38 extends around the bottle 12 and the ring 38 is coextensive with the top end 18 of the bottle 12. The ring 38 has an inwardly facing side 40 and the inwardly facing side 40 is beveled. In this way the inwardly facing side 40 enhances comfort for the penis. Additionally, the ring 38 is comprised of a resiliently compressible material to enhance comfort for the user.

A saddle 42 is coupled to the ring 38 and the penis is positioned on the saddle 42 when the penis is inserted into the bottle 12. In this way the saddle 42 inhibits the penis from being abraded. The saddle 42 extends into the bottle 12 to direct the penis into the bottle 12 for urine collection. Additionally, the saddle 42 is concavely arcuate with respect to the top end 18 of the bottle 12. The saddle 42 may be comprised of a resiliently compressible material for enhancing comfort for the user.

In use, the user inserts the user's penis into the bottle 12 for urine collection. The penis is positioned on the saddle 42 while the bottle 12 is held for urine collection. In this way the saddle 42 inhibits the penis from being abraded during 38 urine collection. Thus, the user can comfortably urinate into the bottle 12 when the user is bedridden, confined to a wheelchair or otherwise incapable of using a traditional bathroom. Additionally, the bottle 12 may be employed in a medical environment to collect urine for analysis or the like.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A contoured urinal assembly being configured to receive a penis for urination without abrading the penis, said assembly comprising:

a bottle having an angled neck wherein said bottle is configured to facilitate a user to insert the user's penis into said angled neck for urine collection;

a handle being coupled to said bottle for gripping;

a ring extending around said bottle, said ring being comprised of a resiliently compressible material said ring having an inwardly facing side; and a saddle being within the bottle beginning from the inwardly facing side of said ring and integral to said ring, said saddle being elongated extending away from said inwardly facing side of said ring into said bottle such that said saddle is configured for having the penis positioned thereon wherein said saddle is configured to inhibit the penis from being abraded, said saddle extending from a portion of said ring into said bottle wherein said saddle is configured to direct the penis into said bottle and support a shaft of the penis on the saddle while the penis is inserted into the bottle for urine collection.

2. The assembly according to claim 1, wherein:

said bottle has a bottom end, a top end and an outer wall extending therebetween, said top end being open into an interior of said bottle wherein said top end is configured to having the penis positioned therein, said outer wall being curved between said bottom end and said top end such that said top end lies on a plane being angled with said bottom end;

said outer wall has ounces indicia being printed thereon comprising a graduated scale for measuring fluid volume in fluid ounces; and said outer wall has cubic centimeter indicia being printed thereon comprising a graduated scale for measuring fluid volume in cubic centimeters.

3. The assembly according to claim 2, wherein said ring is coextensive with said top end of said bottle, said ring having an inwardly facing side, said inwardly facing side being beveled.

4. The assembly according to claim 2, wherein said saddle has an inwardly facing surface which is convexly arcuate with respect to said top end of said bottle.

5. A contoured urinal assembly being configured to receive a penis for urination without abrading the penis, said assembly comprising:

a bottle having an angled neck wherein said bottle is configured to facilitate a user to insert the user's penis into said angled neck for urine collection, said bottle having a bottom end, a top end and an outer wall extending there between, said top end being open into an interior of said bottle wherein said top end is configured to having the penis positioned therein, said outer wall being curved between said bottom end and said top end such that said top end lies on a plane being angled with said bottom end, said outer wall having ounces indicia being printed thereon comprising a graduated scale for measuring fluid volume in fluid ounces, said outer wall having cubic centimeter indicia being printed thereon comprising a graduated scale for measuring fluid volume in cubic centimeters;

a handle being coupled to said bottle for gripping, said handle extending away from said outer wall of said bottle, said handle extending toward said bottom end of said bottle;

a ring extending around said bottle, said ring being coextensive with said top end of said bottle, said ring having an inwardly facing side, said inwardly facing side being beveled wherein said inwardly facing side is configured to enhance comfort for the penis, said ring being comprised of a resiliently compressible material; and a saddle being within the bottle and integral to said ring, said saddle beginning from the inwardly facing side of the ring being elongated extending away from said inwardly facing side of said ring into said bottle such that said saddle is configured for having the penis positioned thereon wherein said saddle is configured to inhibit the penis from being abraded, said saddle extending from a portion of said ring into said bottle wherein said saddle is configured to direct the penis into said bottle and support a shaft of the penis on the saddle while the penis is inserted into the bottle for urine collection, said saddle has an inwardly facing surface which is convexly arcuate with respect to said top end of said bottle.

\* \* \* \* \*